United States Patent [19]

Wiley et al.

[11] 4,154,672
[45] May 15, 1979

[54] STANDARDIZATION OF PENETRATING RADIATION TESTING SYSTEM

[75] Inventors: Philip A. Wiley, Boxboro; Herbert L. Aronson, Newton, both of Mass.

[73] Assignee: Bedford Engineering Corp., Bedford, Mass.

[21] Appl. No.: 792,061

[22] Filed: Apr. 28, 1977

[51] Int. Cl.² .................... B07C 5/344; B07C 5/346
[52] U.S. Cl. .................... 209/589; 209/592; 209/905; 250/252; 250/273; 250/277 R
[58] Field of Search .................... 209/73, 74 R, 74 M, 209/111.5, 111.6, 111.7 R, 111.7 T, 121; 250/252, 272, 273, 277 R, 278; 330/25, 96

[56] References Cited

U.S. PATENT DOCUMENTS

| | | | |
|---|---|---|---|
| 2,885,557 | 5/1959 | Kizaur | 209/111.5 X |
| 2,939,960 | 6/1960 | Gunn | 250/252 |
| 3,198,944 | 8/1965 | Furbee | 250/272 |
| 3,361,911 | 1/1968 | Kowalczyuski | 250/272 |
| 3,382,975 | 5/1968 | Hoover | 209/111.6 X |
| 3,880,750 | 4/1975 | Butler et al. | 209/111.7 R |
| 4,009,376 | 2/1977 | Faraguet | 250/252 X |
| 4,060,726 | 11/1977 | Luitwieler et al. | 250/252 |

Primary Examiner—Joseph J. Rolla
Attorney, Agent, or Firm—Schiller & Pandiscio

[57] ABSTRACT

Standardization is provided to control system gain of a penetrating radiation testing system by periodically inspecting a reference object in the same manner as the product samples so as to generate a stabilization signal which is compared to a reference signal. The difference, if any, between the stabilization signal and the reference signal is integrated and the integrated signal is used to correct the gain of the system.

24 Claims, 7 Drawing Figures

STANDARDIZATION OF PENETRATING RADIATION TESTING SYSTEM

The present invention relates generally to inspection systems utilizing penetrating radiation and more particularly to a new and improved apparatus for and method of standardizing such systems.

Inspection systems which make use of penetrating radiation for determining certain properties such as thickness, density or mass of a mass-produced product sample are well known. Typically, the product samples are conveyed into an inspection station, one at a time and exposed to the penetrating radiation. A detector is positioned so as to receive typically either non-absorbed or scattered radiation from the sample. The nature of the radiation depends on the type of measurement made. The detector provides a signal representative of the radiation received by the detector whereby the signal can be processed or interpreted depending upon the type of measurement being made. The signal output of the system sometimes has a tendency to change, due to source variations, as well as detector drift, both usually incurred as a result of temperature and time variations. Other causes of output changes arise from changes in the gain of signal amplification loops and the effect of power supply variations with time, temperature and line voltage. In certain applications, these variations in output can be on approximately the same order of magnitude as the system output signal for the measured property, thereby providing substantial error. To rectify this problem, the prior art devices employ standardization techniques whereby the system output is from time-to-time established to standard values. Such techniques can be relatively time-consuming where standardization is performed in an iterative manner by repetitively pulling the system from its testing position and adjusting for source and zero standardization. Other types of standardization approaches are known. See, for example, U.S. Pat. No. 3,729,632, issued Apr. 24, 1973 to Cho et al where a linearizing network is used to provide standardization.

It is an object of the present invention to provide a system and technique for quickly and automatically standardizing the output of such an inspection system.

It is an additional object of the present invention to provide a system and technique of periodically standardizing the signal output of systems of the type which use penetrating radiation to inspect mass-produced product samples without substantially interrupting the inspection procedure.

Yet another object of the present invention is to provide an improved apparatus and technique for standardizing the signal output of mass-measuring inspection systems of the type employing penetrating radiation.

These and other objects of the present invention are achieved by periodically inspecting a reference object in the same manner as the product samples so as to generate a stabilization signal which is compared to a reference signal. The difference, if any, between the stabilization signal and the reference signal is preferably integrated and the integrated signal is used to control system gain.

Other features and many of the attendant advantages of the invention are disclosed in or rendered obvious by the following detailed description which is to be considered together with the accompanying drawings in which.

In the drawings, like numerals are used to refer to like parts.

Figure 1:
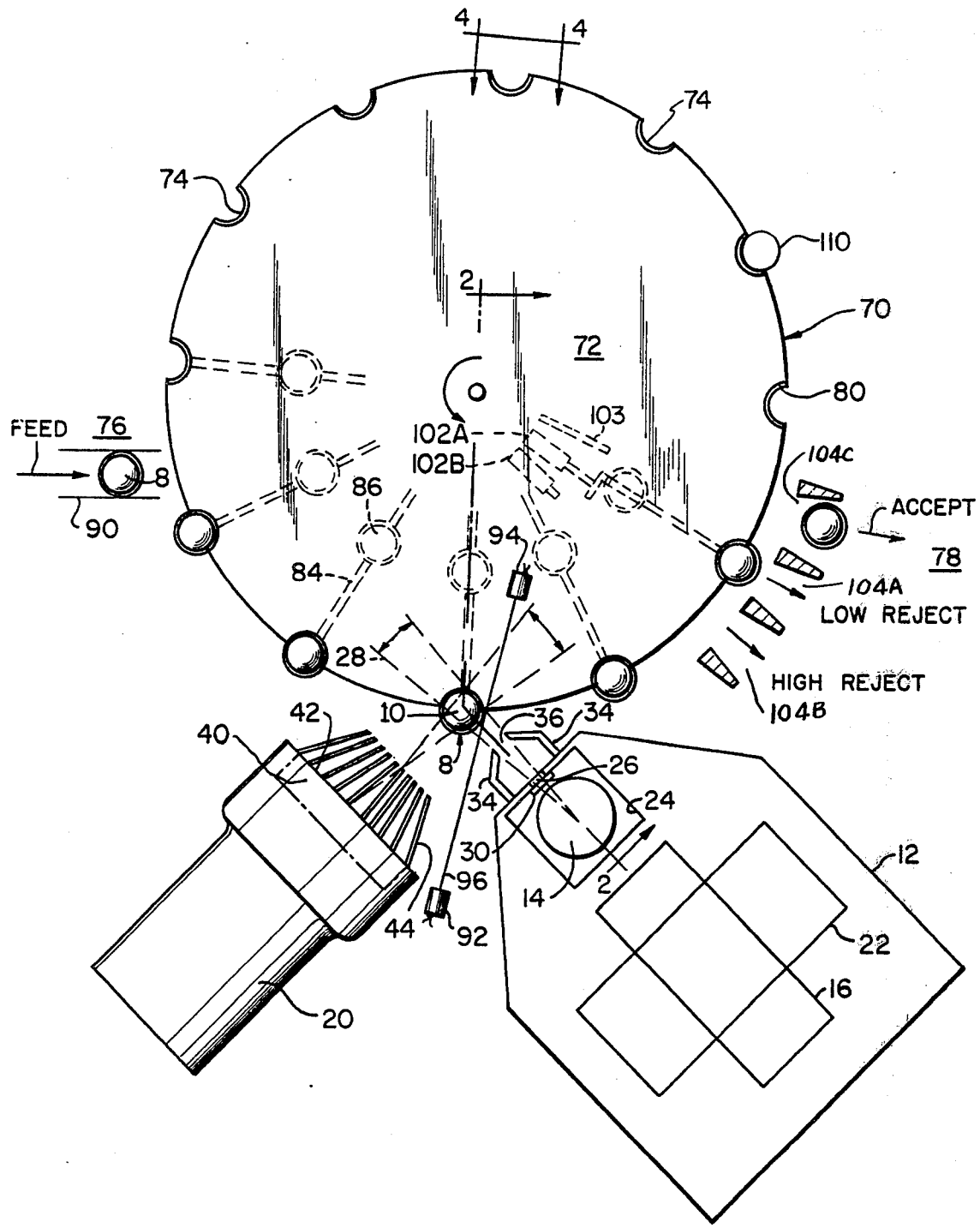
FIG. 1 is a top view of one embodiment of a product-mass measuring system including a detector providing an analog output signal and incorporating the principles of the present invention.

Referring to the drawings, the present invention is described with reference to an embodiment of an inspection apparatus preferably forming part of a system for determining whether the mass of the contents of a product sample, such as an ammunition cartridge or a medicinal capsule, is within predetermined limits. It will be obvious, however, that the invention can also be used in other inspection systems, such as those used to determine the thickness or density of a material.

Figure 2:
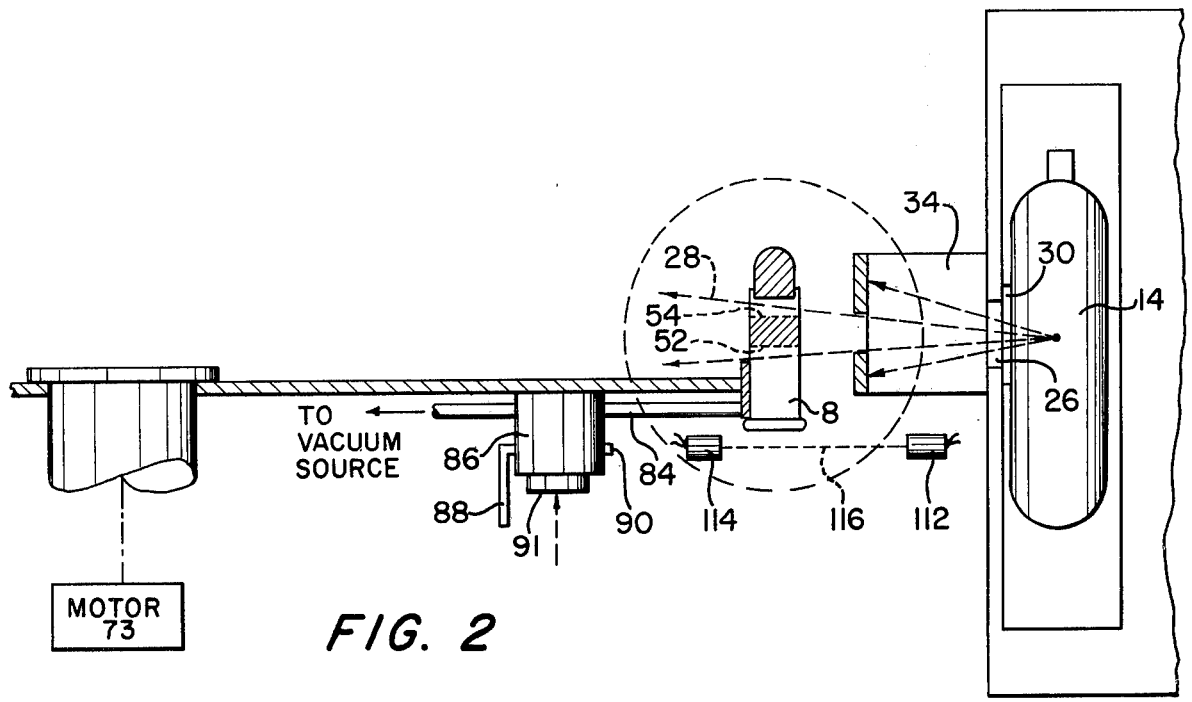
FIG. 2 is a sectional view of the apparatus taken along line 2—2 in FIG. 1 with a product sample positioned for inspection.
Figure 3:
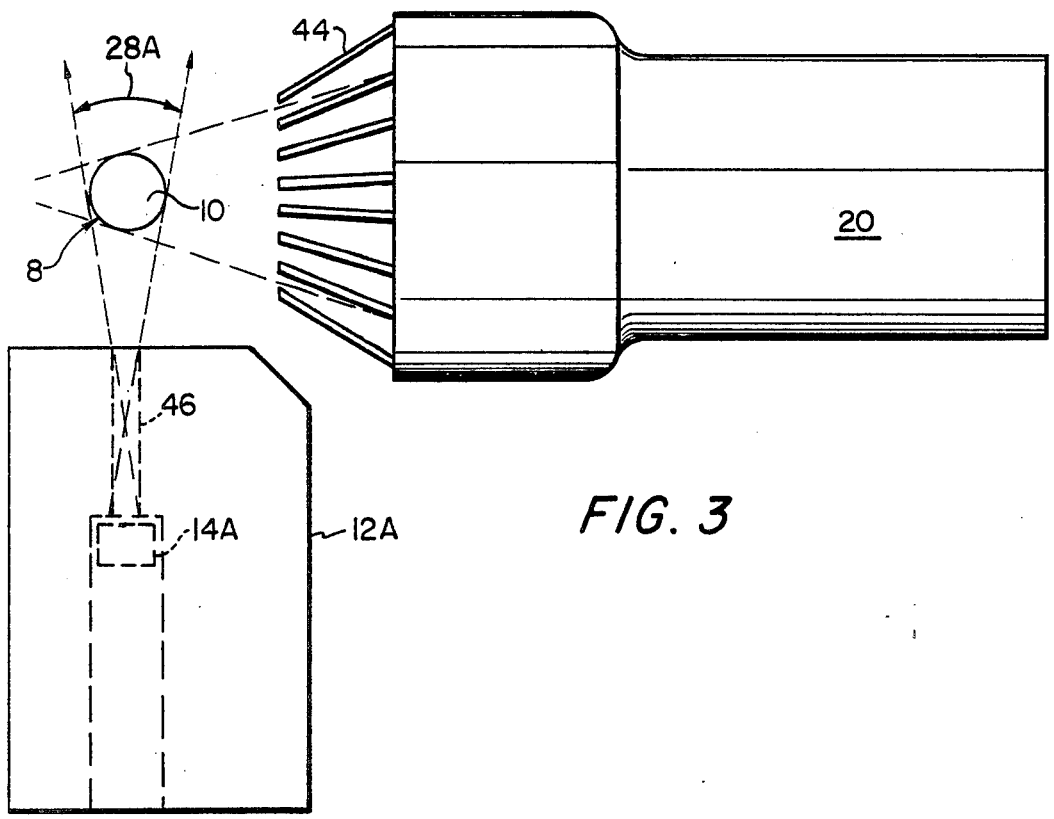
FIG. 3 is a top view of an embodiment of a product-mass measuring system including a detector providing a digital output signal and incorporating the principles of the present invention.
Figure 4:
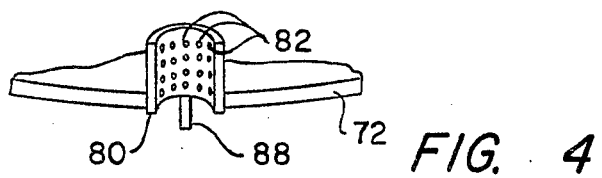
FIG. 4 is a partial perspective view taken along line 4—4 in FIG. 1.

More specifically, referring to FIGS. 1, 2 and 4, the apparatus shown comprises a housing 12 for supporting a source 14 of electromagnetic radiation, a pulse transformer 16 energized by the power supply 18 (shown in block form in FIG. 6) for energizing the source 14, and a radiation detector 20. Housing 12 includes a supporting structure 22 for supporting transformer 16, a chamber 24 in which is supported source 14, and an aperture 26 which is positioned so as to allow a beam 28 of radiation emitted by the source 14 to pass out from chamber 24 to the inspection point 10. Source 14 is preferably any one of several devices for producing low-energy X-rays or low-energy gamma radiation, such as an X-ray tube (as illustrated, for example, in McGraw-Hill Encyclopedia of Science and Technology, McGraw-Hill Book Company, Inc., (1960), Vol. 14, pp. 587–590) or a container filled with Americium 241, Gadolium 143 or Cobalt 57. In the embodiment shown in FIGS. 1 and 2, source 14 is an X-ray tube which is turned on selectively for a predetermined amount of time in order to irradiate a product sample 8 at point 10 with a predetermined amount of radiation. However, as described in greater detail hereinafter with reference to FIGS. 3 and 7, source 14 can also be of a type which radiates the beam 28 continuously, with the product sample 8 moving into the path of the beam for a predetermined period of time. As is well known in the art, chamber 24 can be filled with oil in order to prevent overheating of source 14. A thin wall window 30, transparent to beam 28 and impermeable to the oil, is positioned over the aperture 26 so as to prevent oil leakage. One suitable material for the window is black nylon, although other materials will be obvious to those skilled in the art.

The front of housing 12 is provided with a baffle and collimator assembly which includes two opposing plates 34, each attached in any suitable manner along one edge to housing 12 and contoured and spaced from one another at the other end to form the slit aperture 36. The latter is aligned with aperture 26 and contoured to shape beam 28 so that the beam substantially conforms to a predetermined cross-sectional shape and illuminates either all or a predetermined portion of the product sample 8 positioned at point 10. The beam preferably has a width in the region of point 10 which does not significantly exceed the width of product sample 8, as seen in FIG. 1. The plates 34 of the baffle assembly are opaque to the radiation of beam 28. Hence, any radiation emitted through aperture 26, toward either plate, will be blocked by that plate.

Detector 20 is positioned so as to measure radiation scattered by the product sample 8 positioned at or passing through point 10, when the product sample is irradiated by beam 28. Detector 20 preferably is located as close as possible to housing 12 and may be, although not necessarily, attached to the housing so as to provide a compact structure. The particular angular position of the detector 20 relative to the source 14 is not absolutely critical to the measurement of the mass of the product sample since scattering of radiation occurs over a wide angle. However, it is desirable to position the detector so that it substantially receives only scattered radiation from the product sample and none directly from the source. Detector 20 is sensitive to the radiation scattered by the product sample 8 at point 10 and, in the case of pulsed X-rays, converts the radiation received into an analog electrical current or voltage signal. The magnitude of this signal is a function of the amount of scattered radiation received which in turn is a function of the mass of the product irradiated. As described in greater detail with reference to FIGS. 3 and 7, in the case of some low activity sources detector 20 converts the radiation received into a series of digital pulses, the pulse repetition rate being dependent on the amount of radiation received. Accordingly, detector 20 may be any one of various devices such as an ionization detector or scintillation counter, depending upon the nature of the radiation emitted by source 14. Preferably, detector 20 includes a photomultiplier tube (not specifically shown) operated in a current mode and positioned behind a sodium iodide scintillation crystal 40 which is mounted to the photomultipler tube behind a window 42. The latter is made of a material which is transparent to the scattered radiation received from the product sample 8 at point 10. Preferably, window 42 is made of black nylon or other similar material. A collimator assembly 44 which is made of a material, such as lead or tungsten, which will not excite or amplify the scattered radiation received from point 10, is positioned in front of the window 42 and shaped so as to pass scattered radiation from the product sample 8 positioned at point 10 and also to prevent any of the direct radiation of beam 28 from passing directly through the scintillation crystal 40. Preferably, although not necessarily, the collimator assembly 44 is shaped and contoured so as to have a limited angle of view of the product sample 8 positioned at point 10 so as to pass scattered radiation from only a selected portion of the product sample at point 10, as will be more evident hereinafter.

FIG. 3 shows a modification of the embodiment of the present invention and is substantially the same as the embodiment shown in FIGS. 1 and 2, except that a low activity gamma ray source 14A, such as Cobalt 57 or Americium tube 41 has been substituted for the X-ray tube 14. Source 14A is placed within the housing 12A, the latter being provided with an elongated aperture 46 so as to function as a collimator to define the shape of the beam 28A of gamma radiation. In such a situation detector 20 is turned on for a predetermined period of time while a product sample is exposed at the inspection point 10 or alternative means, such as shutter (not shown), may be used to intercept the beam 28A in order to prevent the beam from passing through point 10 at all times, and for exposing each product for a predetermined period of time.

In accordance with one measuring technique, the beam 28 of both embodiments floods the product sample positioned at point 10 so that the entire or a selected portion of the bulk of the product is substantially instantaneously exposed to the beam. The detector 20 receives radiation scattered by the product when the latter is irradiated by beam 28 and generates an electrical signal representative of the quantity of scattered radiation which is received. In the case of the embodiment of FIGS. 1 and 6, where a high activity source is used, this signal will be analog in nature. Where the source is of low activity, such as that used in the system shown in FIGS. 3 and 7, the signal will be in the form of a series of digital pulses. By properly processing and evaluating the signal output of the detector 20 of either system, the mass of the product positioned at point 10 can be easily calculated.

Any one of various systems known to those skilled in the art may be provided for conveying samples 8 sequentially to point 10 so that the mass measurement can be made. Further, any means may be provided for sorting the products in accordance with their measured mass.

For example, a transport system is shown in FIGS. 1 and 2 in the form of a carousel-type conveyor 70 which has particular utility for conveying samples such as ammunition cartridges 8 to the inspection point 10 and subsequently away from this point after the mass measurement is made. Briefly, the carousel conveyor 70 comprises a rotatable turntable, shown schematically at 72, rotated by means such as motor 73, and having means for holding the cartridges at a predetermined circumferential distance from one another so that as the turntable rotates, only one cartridge is exposed to the beam 28 at a time. The means for holding the cartridges may comprise a plurality of semi-cylindrical slots 74 formed around the periphery of the turntable 72 and a flexible, elastic retaining belt (not shown) for holding each cartridge in a slot in a substantially rigid manner. With this arrangement, the cartridges can be individually, manually mounted in each of the slots 74 at loading point 76, which is clear of beam 28, and subsequently removed at the sorting point 78, also clear of beam 28, after the inspection of the cartridge is made.

Alternatively, the means for holding each cartridge to the turntable may include vacuum means for holding the products to the periphery of the turntable 72. More particularly, referring to FIGS. 1, 2 and 4, each slot 74 is provided with a cartridge-receiving holder 80 provided with a plurality of small holes 82 through which air can be drawn into the tube 84. Each cartridge 8 can be held by a corresponding holder by applying a vacuum through tube 84. Each tube 84 is provided with a pressure-release valve 86 which is normally in a closed position. Each valve 86 is suitable connected to a lever 88 which preferably extends in a vertical direction down from the turntable when valve 86 is in the closed position and is rotatable with the valve 86 about the pivot pin 90 so as to open the valve. Each tube 86 is suitably connected to a vacuum source (not shown) which provides a sufficient vacuum to each of the holders 80 so that the latter can hold a cartridge regardless of whether the other holders are holding similar cartridges so long as the valve 86 associated with the particular holder is closed. When the associated valve is open, air is drawn into line 84 through a vent port 91 in the valve, preventing the application of a vacuum to the holes 82 of the corresponding holder and resulting in the cartridge being released. It will be appreciated that each holder 80, tube 84, valve 86, lever 88, as well as the turntable 72 itself, are all suitably positioned so as to be outside of and not exposed to the beam 28, whereby no appreciable amount of scattered radiation from them will be detected by the detector 20.

Other types of rotating turntables including vacuum means for holding products along its periphery are known, for example see U.S. Pat. Nos. 3,366,236, 3,709,598 and 3,838,766. Other conveying means are well known in the art. For example, each cartridge can be conveyed on a chain link conveyor. The latter type of conveying device is capable of transporting up to 1200 cartridges a minute through the inspection point 10. This latter type of device is preferred with the X-ray embodiment of FIGS. 1 and 2. When operating at such a high rate of inspection the conveyor may be operated so that it moves at a constant speed whereby the cartridges pass one at a time through the inspection point 10 at preselected time intervals. Alternatively, however, where slower inspection times are required such as those required with the low activity sources provided in the embodiment of FIG. 3, the conveying means may be operated so that it moves the individual cartridges intermittently, indexing a new cartridge into position at point 10 each time the conveyor is operated. In the latter situation, motor 73 is preferably a stepping motor, such motors being well known in the art.

The cartridges may be automatically attached to the turntable at the loading point 76. For example, the cartridges may be fed through a suitable feeding mechanism 90 (shown schematically in FIG. 1) at point 76 which may be a spring loaded magazine which spring biases loaded cartridges against the edge of the turntable. As the turntable rotates, each slot 74 contacts a cartridge and the vacuum is applied through the holder 80 to hold the particular cartridge to the turntable until the cartridge has been inspected.

A detector system (see FIG. 1) is provided for determining when a cartridge is positioned at point 10. This system comprises a light source 92 and a light detector 94 disposed at opposite sides of the path travelled by the cartridges 8 through the inspection point 10. The detector operates in a manner well known to those skilled in the art; light source 92 directs a light beam 96 toward light detector 94. When a cartridge moves into position at point 10, it interrupts beam 96, so that the light detector 94 provides a signal to a control circuit, e.g. unit 100A in FIG. 6, which in turn triggers the operation of the source 14.

Each cartridge which passes through point 10 and is measured can subsequently be collected in three separate groups as follows:
(1) product samples whose mass is within some predetermined range; (2) samples whose mass is below the predetermined range; and (3) samples whose mass is above the predetermined range.

When the individual samples are loaded, for example, on the conveying system manually, the sorting may also be accomplished manually. However, it will be appreciated that the sorting system may also be automatic. For example, referring to FIG. 1, automatic sorting means are provided in the form of two reject solenoids 102A and 102B and the accept shaft 103. Each solenoid is positioned below the turntable 72 and is selectively energizable so that its movable shaft or armature extends into the path of the individual levers 88 as the latter rotate with the turntable 72. The shaft 103 is fixed and positioned to intercept the individual levers 88 after they have passed the solenoids. The levers pivot when contacting anyone of the shafts 102 of an energized solenoid or the fixed shaft 103, causing the corresponding valve 86 to open thereby releasing the cartridge. Two separate chutes 104A and 104B are provided for receiving cartrdiges released by the energization of the corresponding solenoids 102A and 102B and a third chute 104C receives cartridges released by shaft 103 when neither of the solenoids is energized. The chutes respectively lead to three bins which correspond to the three classification groups.

The inspection system thus described is useful in determining the mass of each product sample 8 conveyed into position at the inspection point 10 so long as the output of detector 20 accurately corresponds to the mass of the sample exposed. However, for the same mass, the output of the detector can vary due to a variety of variables including (1) variations in the amount of radiation provided by source 14 due to time and temperature variations; (2) detector drift brought about by the nonuniformity of the input-output characteristics of detector 20 due to time and temperature variations; (3) changes in the gain of signal amplification loops; and (4) variations in the power provided to the radiation source 14 and detector 20 arising from time, temperature and line voltage variations.

Figure 5:
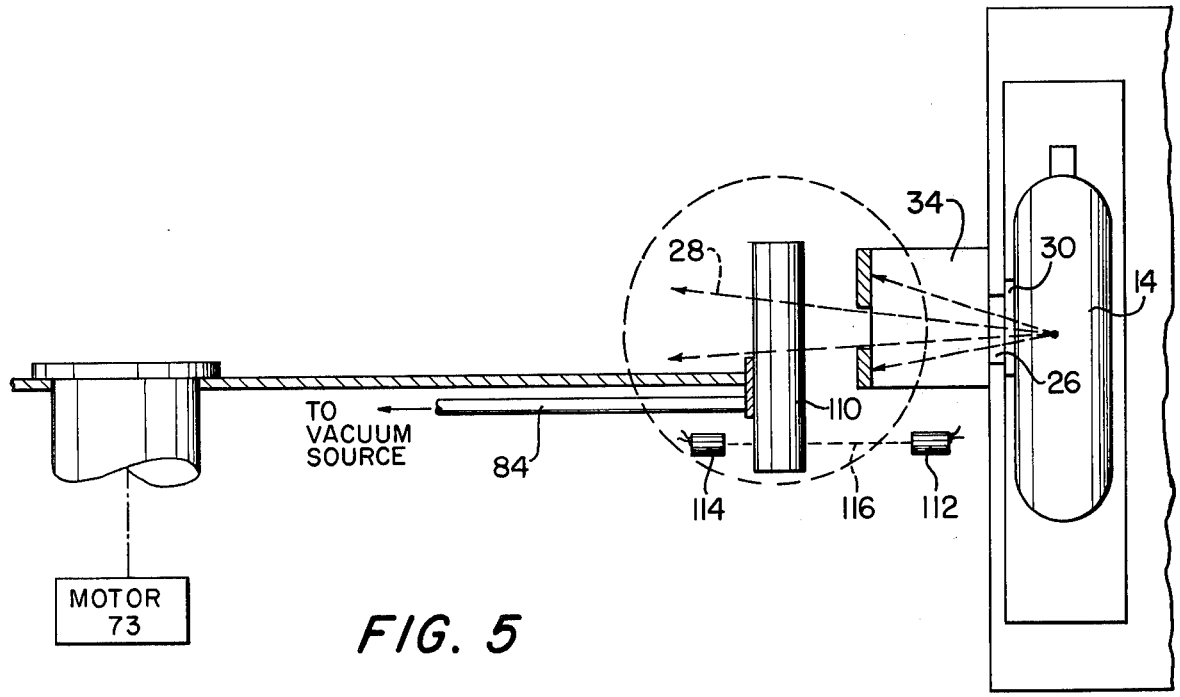
FIG. 5 is a sectional view of the apparatus taken along line 2—2 in FIG. 1 with a reference object positioned for inspection.

Referring to FIG. 1, and more particularly FIG. 5, in accordance with the present invention, a reference object 110 is periodically inspected in the same manner as each product sample 8. Since the system thus described is designed to measure the mass of each sample 8, object 110 is designed so that the portion of the object exposed to beam 28 and providing scattered radiation to detector 20 is of a predetermined mass. As shown, the object 110 is attached, in any known manner, to the turntable 72 of the conveyor 70 in one of the slots 74 between two product samples 8. The object, for example, may be held by vacuum in one of the holders 80, in which case the release valve 86 is made inoperative by either omitting the valve or omitting the portion of lever 88 extending into the path of the shafts of the energized solenoids or the shaft 103. The object may be a selected one of the product samples 8 having a known mass, or it may be a different type of object made of a different material. For example, where ammunition cartridges are being inspected with a low energy X-ray or gamma ray source, object 110 should be made of a low density material, such as aluminum or a plastic such as one of the methacrylate ester polymers manufactured under the trademark Lucite.

As shown in FIGS. 2 and 5, a reference object detector system is provided for determining when a reference object 110 is positioned at point 10, as distinguished from a product sample 8. This system comprises a reference object light source 112 and a reference object light detector 114 disposed at opposite sides of the path traveled by the reference object 110 through the inspection point 10. The source 112 and detector 114 operate in the same manner as the light source 92 and detector 94, wherein source 112 directs a light beam 116 toward the detector 114. The beam 116 however, is disposed in a plane through which the product samples 8 do not pass so that the samples will not interrupt the beam 16 as they pass through the inspection point 10. Means are therefore provided for interrupting the beam 116 only when the object 110 is located at the point 10. The means may be for example, a portion of the object 110 itself, which extends through the plane through which the beam 116 passes (as shown in FIG. 5), or alternatively, may be an object provided on the turntable 72, such as a projecting pin or the like. In any event, as the object 110 moves into position at point 10, the beam 116 is interrupted so that the detector 114 provides a signal to the control circuit 100 (See FIGS. 6 and 7) to indicate to the circuit the presence of the reference object 110. Object 110 also interrupts beam 96, so that the light detector 94 provides a signal to the control circuit 110 which in turn triggers the operation of the source 14.

The exposure of the reference object 110 and the detection of scattered radiation from the object by detector 20 occurs in the same manner as each sample 8 when it is positioned at point 10. The signal output provided by detector 20, hereinafter called the stabilization signal is representative of the mass of the portion of the object 110 exposed. Unlike signals provided by the exposure of each of the samples 8, the stabilization signal is compared to a reference signal having a predetermined value. Where system gain remains constant, the stabilization signal will remain substantially constant relative to this reference signal. Where system gain however varies, the comparison of the stabilization and reference signals can be used to control the system gain. This system gain control is maintained constant between each stabilization measurement by employing integration techniques.

The foregoing becomes more evident with an understanding of the control circuits 100A (FIG. 6) and 100B (FIG. 7) and their operation.

Figure 6:
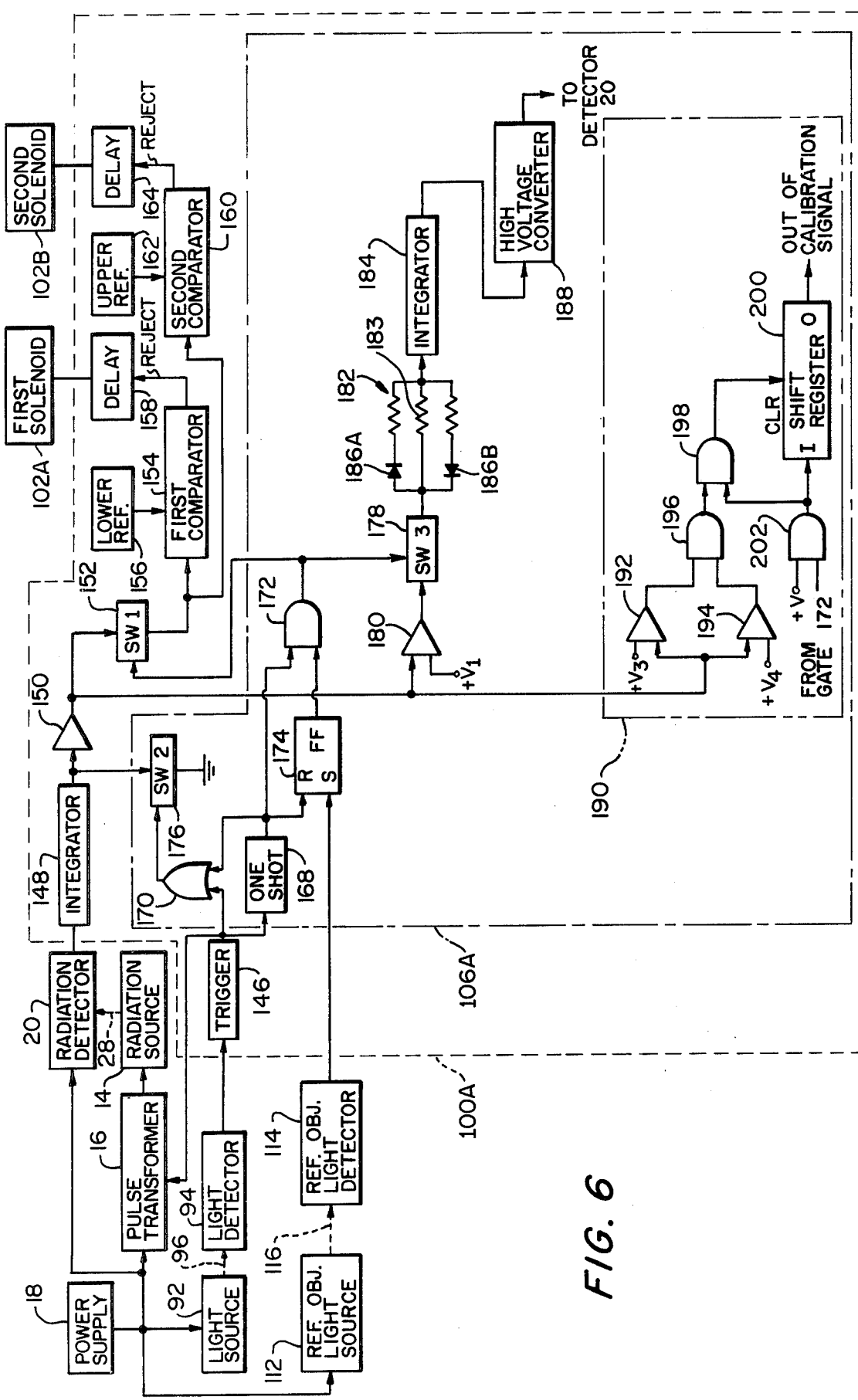
FIG. 6 is a block diagram of a complete system of the analog signal type which embodies the principles of the present invention.

Referring to FIG. 6, a control circuit 100A useful with a detector providing an analog signal output is shown. The system comprises means for measuring the mass of each product sample 8 and subsequently classifies each in accordance with its measured mass, and means 106A for stabilizing the system gain. Specifically, the power supply 18 is connected to the pulse transformer 16, radiation detector 20 and light sources 92 and 112. Light detector 94, coupled to the light source 92 by the beam 96, provides an output to a trigger circuit 146. The output of trigger circuit 146 is connected to pulse transformer 16 which in turn is connected to radiation source 14. Trigger circuits are well known to those skilled in the art. Trigger circuit 146 operates such that when the light beam 96 is broken and the detector 94 provides an output to the trigger circuit, the latter will provide an output pulse to the transformer 16. This causes source 14 to energize briefly, whereby a beam 28 is generated for a brief time, e.g. 5 milliseconds, from the X-ray tube. Detector 20 detects radiation scattered by the product sample positioned at point 10. The detector 20 preferably operates in a current mode and hence will provide an analog current output which contains energy, the magnitude of which is indicative of the mass of the product sample positioned at point 10. In a manner well known in the art, this current output signal is integrated by an integrator 148 to provide a signal whose magnitude represents the amount of radiation energy received by detector 20 and thus a measure of the mass of the product sample at point 10. Integrators are well known in the art and thus will not be described in detail. For example, the integrator can include an RC circuit in which the amount of energy in the output signal from detector 20 is stored in a capacitor and this amount of energy is measured in the form of a voltage. The signal output of integrator 148 is connected to the input of amplifier 150, which in turn provides a signal through the switch circuit 152 to the first and second comparators 154 and 160, respectively. The switch circuit 152 is normally closed, i.e. the output of amplifier 150 is connected to the input of the first and second comparators, except when the mass of the reference object is being measured. In the latter instant, a signal is received from AND gate 172 of the stabilizing means 106A (described in greater detail hereinafter) opening switch 152 so that the output of amplifier 150 is not applied to either comparator. When the switch circuit 152 is closed, the amplified signal from amplifier 150 is compared to a lower reference signal provided by a lower reference source 156. The lower reference signal is representative of the lower limit of the range of acceptable masses plus the mass of any environmental structure exposed by beam 28 as well as the average mass of each container, if appropriate, in which the product mass being measured is contained, e.g. the mass of product in an empty state. This lower reference signal is generated in a suitable manner, e.g. by dropping off a suitable voltage or current from a variable voltage or current divider network, and its end is set to equal the level of the output of integrator 148 resulting from irradiating an empty product container at point 10 with beam 28.

If the magnitude of the signal provided by integrator 148 and amplifier 150 is less than the lower reference signal, the output of the first comparator 154 is a reject signal. The reject signal can be indicated to the operator in the form of an individual indication light (not shown) or suitably delayed by time delay 158 so as to energize solenoid 102A in order to release the product sample from the carousel when the product sample is adjacent the chute 104A leading to the bin receiving those cartridges with an insufficient amount of powder. If, however, the signal provided by the amplifier 150 is equal to or above the lower reference signal set by the lower reference source 156, the comparator 154 will not provide a reject signal and the solenoid 102A will not be energized.

The output of the amplifier 150 is also applied to the second comparator 160 where the amplifier output is compared with an upper reference signal from an upper reference signal source 162. The upper reference signal provided by source 162 is representative of the maximum amount of acceptable mass of material contained in any product sample including the average mass of any environmental structure and container (if appropriate). If the magnitude of the accept input signal to the second comparator 160 is above the upper reference signal, comparator 160 will provide a reject output signal to a suitable visual indicator (not shown) for the operator or to time delay 164 which in turn energizes solenoid 102B so as to release the sample when it is adjacent chute 104B leading to the bin receiving those samples with an excess amount of material. If however, the signal provided by the amplifier 150 is equal to or below the upper reference signal set by the upper reference source 162, the comparator 160 will not provide a reject signal and the solenoid 102B will not be energized.

On the other hand, if the amplified signal input to the second comparator 160 is below the upper reference signal provided by the source 162, this may be indicated to the operator as an acceptable sample by a suitable indicator (not shown) operated by a signal produced by the output of the two comparators. Preferably, as shown, if the signal is above or equal to the lower reference signal established by the source 156 and below or equal to the upper reference signal established by the source 162, neither solenoid 102A nor 102B is energized, and lever 88 is contacted and pivoted by the shaft 103 as it rotates past the solenoids 102A and 102B, so as to release the sample when it is adjacent chute 104C leading to the bin receiving acceptable samples. It will be appreciated that where an automatic sorting system is provided and several samples are positioned between the current sample being inspected and the sample to be sorted, suitable means other than the delays 158 and 162 can be used. For example, electrical storage means such as a storage register can be used to store the classification of a particular sample until it is ready to be sorted. The number of signals stored in such a shift register will be equal to the number of samples between the sample being inspected and the sample to be sorted. These signals are stored and shifted one by one so that the sample at sorting point 78 can be properly sorted. Alternatively, mechanical means such as a camming mechanism may be provided which is adapted to follow each sample and release the sample into the appropriate chute.

The means 106A for stabilizing the system gain will now be described. The output of trigger circuit 146 is connected to the input of OR gate 170 and to an input of a one-shot 168, while the output of the latter is connected to a second input of OR gate 170. One-shots are well known in the art and generally provide a pulse of a predetermined duration when a pulse is provided at its input. Thus, one-shot circuit 168 provides a positive pulse of a predetermined duration when a pulse is provided by the trigger circuit 146. OR gates also are well known in the art and generally provide a high logic signal at its output when any one or all of its inputs are high and a low logic signal only when all of its inputs are at a low logic level. The output of OR gate 170 is connected to a second switching circuit 176, the latter being connected between the output of integrator 148 and ground so as to clear the integrator 145 after each product sample 8 is inspected at point 10 and before the next sample is tested. The switching circuit 176 is generally closed (connecting the output of integrator 148 to ground) when the input to the switching circuit from OR gate 170 is low, and opened (so that the output of the integrator 148 is provided to the input of amplifier 150) when the output of OR gate 170 is high.

The output of the one-shot 168 is additionally connected to an input of AND gate 172 (which in turn has its output connected to a third switching circuit 178) and to the reset input of the RS flip-flop 174 (the latter having its output connected to a second input of AND gate 172). The set input of the RS flip-flop 174 is connected so as to receive the output signal from the reference object light detector 114, the latter being coupled to the light source 112 by the beam 116. The output of flip-flop 174 goes high when the beginning (positive-going transition) of the output signal of the reference object detector is received at the set input of the flip-flop and will remain high until the end (negative-going transition) of the pulse output of the one-shot 168 is received at the reset input, whereupon the output of the flip-flop will go low.

The output of amplifier 150 is connected to one input of the differential amplifier 180. The other input of amplifier 180 is connected to a reference voltage level V1, which voltage level is representative of the mass of the reference object when the system is substantially under stable conditions. Amplifier 180 compares the two voltage signals applied to the inputs and provides an error signal, representative of the difference between its two inputs, at the output. The output of amplifier 180 is connected to the input of the switching circuit 178 which in turn has its output connected to the integrator time constant network 182. The integrator time constant is controlled by the middle resistor 183 except during initial system stabilization (or acquisition) where the diodes 186A and 186B are turned on, resulting in a reduction of the integrator time constant. The switching circuit 178 provides a closed path between the output of amplifier 180 and the network 182 when the output of the AND gate 172 is high. When the output of AND gate 172 is low however, the switching circuit 178 is open circuited between the amplifier 180 and network 182. The output of the network 182 is connected to the input of an integrator 184, and functions to speed the integration process when the error signal provided by amplifier 180 is relatively large. The integrator 184 acts to essentially average out the error signals provided by the amplifier 180 for each reference object measurement so as to essentially exclude high frequency transient fluctuations having very little signal energy from the error signal. The output of integrator 184 is applied to the high voltage DC-to-DC converter 188. The output of converter 188 is preferably applied to the anode of the detector 20 so as to control the gain of the detector 20.

Circuit 106A preferably also includes an out of calibration monitor 190 for providing an indication to the operator when the circuit 106A is not stabilizing the gain of the system. Specifically, the output of amplifier 150 is connected to an input of each of the comparators 192 and 194. The reference inputs of comparators 192 and 194 are set so that they differ by the total amount of acceptable drift. Thus, the lower reference input of comparator 192 is the minimum acceptable level of the signal output of amplifier 150 when the mass of the reference object is measured, while the upper reference input of comparator 194 is the upper limit of the output of amplifier 150 when the mass of the reference object is measured. For example, if one is only concerned with large errors, e.g. a three percent error, the reference voltage levels of the inputs of comparators 192 and 194 are set apart so as to allow up to three percent drift in system gain. The outputs of comparators 192 and 194 are connected to two respective inputs of AND gate 196, the output of the latter being connected to an input of AND gate 198. The output of AND gate 198 is connected to the clear input of the shift register 200. The other input of AND gate 198 is connected to receive the output of AND gate 202. The latter is connected to a positive voltage at one input so that the input is always high, while the other input is connected to the output of AND gate 172. The output of AND gate 202 is also connected to the input terminal of shift register 200, while the output of the shift register is connected to a suitable monitoring signalling device, such as a light or an audio alarm. Shift registers are well known in the art and generally register 200 provides a zero voltage output so long as the register is not full. The register includes a predetermined number of storage bits and each time a pulse is received at the input of the register, the latter shifts the pulses one bit to the next adjacent bit until the register is full. When full the output of the register provides a signal to the operator. All of the bits of the register, however, are cleared when a high logic signal is provided by the output of AND gate 198 to the clearing input of the register. By way of example, if the system is designed to permit 3% drift in system gain and the shift register may have a three-bit capacity, an out of calibration signal is provided when three successive measurements are made in which the error is greater than 3%. For larger errors, however, it may be desirable to reduce the capacity of the shift register (to one or two bits), while for smaller errors, it may be desirable to increase the capacity of the shift register.

In operation, each product sample 8 is conveyed to the inspection point 10 whereupon it interrupts the light beam 96 causing the light detector 94 to provide an output signal. It will be noted that each sample does not interrupt the beam 116 and no signal is provided by the reference object light detector 114 since the beam lies in a different plane from the sample. The output signal of detector 94 is applied to trigger circuit 146, which in turn provides a pulse signal to the pulse transformer 16 causing source 14 to energize briefly. The beam 28 is thereby generated for a brief time to expose the sample, and the radiation scattered is detected by the detector 20. The signal output is passed to the integrator 148, integrated and subsequently amplified by amplifier 150. As will be more evident hereinafter, when a product sample is being inspected and not the reference object 110, the signal output of AND gate 172 will be low so that (1) the switching circuit 152 is closed; (2) the switching circuit 178 is open and (3) AND gate 202 will not provide a pulse to the shift register 200. The output of amplifier 150 is thus applied only to the first and second comparators 154 and 160. The comparisons are made to determine whether the signal applied to the comparators is below the lower reference signal applied by source 156, above the upper reference signal applied by source 162, or in between at some acceptable level. If rejected, the appropriate signal is generated and applied to one of the corresponding delays 158 or 164 and subsequently used to energize the respective solenoids 102A or 102B. When energized, the shaft of the particular solenoid will extend into the path of the particular lever 88 of the valve 86 so that as the carousel rotates into position, the valve is opened allowing air to enter through the port 91 releasing the sample into the appropriate chute 104A or 104B. If the sample is acceptable, neither solenoid is energized and the lever will pivot about shaft 103 releasing the sample into the appropriate chute 104C.

When a pulse is provided by trigger circuit 146, it is applied to an input of the OR gate 170 and to the input of the one-shot 168. The output of the latter is also applied to OR gate 170. The output of OR gate 170 will remain high so long as one or both pulses are provided at the input of the gate. The high output level of the OR gate 170 keeps the switching circuit 176 open for this period of time. At the end of the duration of both pulses, after a measured signal provided at the output of amplifier 150 is applied to the comparators 154 and 160, the output of gate 170 goes low, and the switching circuit closes shorting the output of integrator 148 to ground. This clears the integrator for the next signal.

The sample 8 does not interrupt the light beam 116 so that detector 114 will not provide a signal to the set input of the RS flip-flop 174. Thus, the output of the RS flip-flop, will remain low. The output of AND gate 172 will remain low regardless of the pulse provided by the output of one shot 168 and applied to the other input of the AND gate. Since the output of AND gate 172 remains low, the switching circuit 178 remains open so that the stabilization circuit will be disabled. Similarly, AND gate 202 remains disabled so that the shift register 200 will not count a pulse.

When the reference object 110, however, is conveyed into the inspection point 10, both beams 96 and 116 are interrupted, so that both detectors 94 and 114 provide output signals. In the same manner, as previously described, the output of detector 94 is applied to the trigger circuit 146. The output of the latter provides a pulse signal to the pulse transformer 16 causing the source 14 to energize and generate beam 28. Thus, the reference object 110 is exposed at point 10 and scattered radiation from the object is received by detector 20 producing a signal output which is applied to the integrator 148. The output of the integrator is subsequently applied to amplifier 150.

The output of light detector 114 provides a pulse to the set input of RS flip-flop 174, whereby the output of the latter goes high. During this period, when both the pulse output of one-shot 168 and the output of the RS flip-flop are high, the output of the AND gate 172 will be high. The high output of gate 172 is applied to (1) the switching circuit 152 so that the output of the amplifier 150 will not be applied to the inputs of the first and second comparators 154 and 160, (2) switching circuit 178 so that the latter is closed and (3) the input to the AND gate 202 of the monitor 190.

The output of amplifier 150 is compared to the reference input of the differential amplifier 180. If a difference exists, the amplifier 180 provides an output which is proportional to the difference. The output of amplifier 180 is applied through the closed switching circuit 178, through network 182 to the input of the integrator 184. The integrator 184 integrates the error signal and is transmitted to the high voltage converter 188, where it is amplifier and subsequently applied to the detector 20 so as to control system gain. Simultaneously, to this adjustment of system gain, the output of amplifier 150 is applied to the inputs of the comparators 192 and 194 of the monitor 190. If the signal applied to the comparators is within the permissible error established by the reference signals, both the outputs of comparators 192 and 194 will be high and the AND gate 196 will be enabled. The output of the gate 196 will therefore be high providing a high signal to the input of AND gate 198. Substantially simultaneously, the output of gate 172 enables gate 202. The output of the latter is essentially a pulse, the duration of which is approximately equal to the duration of the pulse provided by one-shot 168. The pulse provided by the output of gate 202 is applied to the input of the shift register 200, where it is registered. It is also applied to gate 198 enabling the latter. When the output of gate 196 is high indicating the output of amplifier 150 is within the permissible drift set by the reference inputs to the comparators, both inputs to gate 198 will be high, and the output pulse will be applied to the clearing input of the register 200, so that the latter is cleared, negating the pulse applied from the output of gate 202 to the input of the register.

If, however, the applied signal from the output of amplifier 150 to the input of comparators 192 and 194, is outside the reference limits, one of the outputs of the comparators will be low so that the AND gate 196 will not be enabled. When this occurs, the output of AND gate 196 remains low so that the output of AND gate 198 will remain low. Thus, no clearing pulse is provided to the shift register 200. The pulse output of AND gate 202 is thereby shifted into the register 200. It will be readily seen that if, for example, register 200 is a three-bit register, and three successive signals are provided at the output of the amplifier 150 which are above or below the permissible limits set by the reference inputs to comparators 192 and 194, the shift register will overflow providing a monitoring signal to the operator indicating that the system gain drifts are not being adequately compensated for.

Finally, as in the measurement of product samples, the output of OR gate 170 will go high during the duration of the pulse outputs of trigger circuit 146 and one-shot 168, whereby the switching circuit 176 will be open to allow the signal to be applied to the input of comparator 180 and the inputs to comparators 192 and 194. At the end of the duration of the pulses the output of OR gate 170 goes low and switching circuit 176 closes shorting the output of the integrator 148 to ground. At the end of a pulse output of one-shot 168, the RS flip-flop 174 is reset so that the output of the latter goes low, disabling the AND gate 172 and opening switching circuit 178. This occurs after the output of the comparator 180 has been applied to integrator 184.

Figure 7:
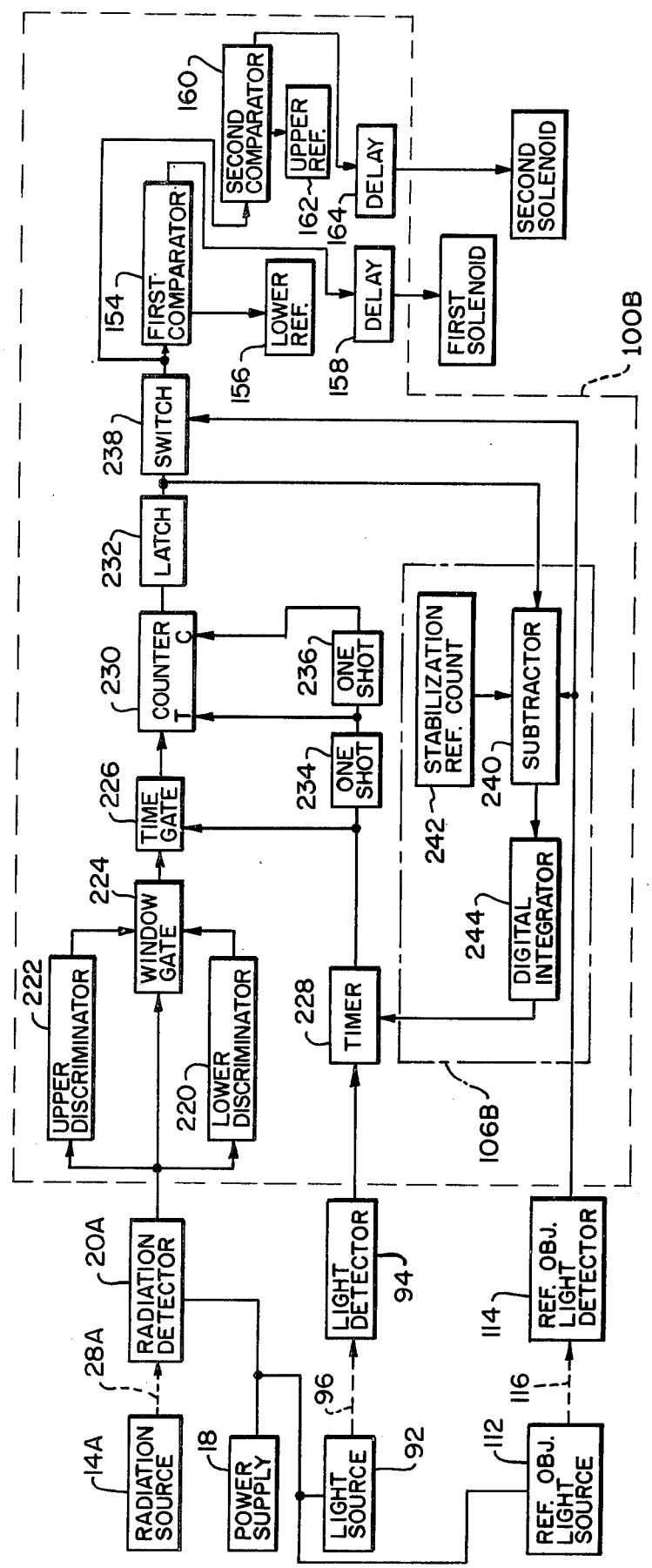
FIG. 7 is a block diagram of a complete system, providing a digital signal type and embodying the principles of the present invention.

Referring to FIG. 7, a control system 100B is described which is useful with a detector of the low activity source type system of FIG. 3. The detector 20A provides an output in the form of a series of digital pulses, the amplitude of each pulse being dependent on the specific isotope used for source 14A and the pulse repetition rate being proportional to the mass of the particular sample or object being inspected. Generally, the system 100B is designed to measure the pulse repetition rate, and thus give an indication of the mass of the particular sample or object being inspected, and utilizes a pulse amplitude discrimination technique which is relatively insensitive to the effects of component drifts with time, temperature and voltage. Further, additional stabilization can be provided by the means 106B for modifying the system gain.

More specifically, the radiation source 14A is shown as continuously providing the low energy beam 28A, so that when a sample 8 or the object 110 is exposed to the beam, scattered radiation is provided to radiation detector 20A. The output of the detector 20A is applied to the inputs of both a lower and upper discriminator 220 and 222, respectively, each of which in turn are connected to the window gate 224. The discriminators generally set the range of amplitudes of the pulses of the output of the detector 20A which will pass through the window gate 224 to the time gate 226. More particularly, the lower discriminator 220 is set so it will pass to the window gate 224 only those pulses whose amplitude exceeds a predetermined level and thus helps to reduce system noise by rejecting those pulses whose amplitudes are below the minimum level. The upper discriminator 222 is set so it will pass to the window gate 224 only those pulses whose amplitudes are below a predetermined maximum level and thus rejects pulses representing higher energy radiation (than that scattered by a sample 8 or object 110) which might be received by detector 20A, such as any energy inadvertently received directly from the source 14A. Where the amplitude of a pulse is within the predetermined limits set by these discriminators 220 and 222, the window gate 224 is enabled so as to transmit the pulse to the time gate 226. The latter is designed to remain closed for a predetermined period of time during which the output of window gate 224 is connected to the input of the digital pulse counter 230. The period of time during which the time gate 226 is closed is dependent on the duration of the enabling time signal received by the time gate from the output of timer 228. Timer 228 is initiated by a signal received from the output of a light detector 94, the latter being activated when the light beam 96, generated by the light source 92, is interrupted.

During the period in which the time gate 226 is closed, the pulses transmitted therethrough are counted in counter 230. The output of counter 230 is a signal representative of the count in the counter and is transferred to the latch 232 when receiving a pulse at its transfer input and is cleared when receiving a pulse at its clearing input. In order to provide the transfer pulse, the end of each signal (the negative-going transition) provided by the timer 228 triggers one-shot 234 which in turn provides the transfer pulse to the counter 230 (after the time gate opens) at the end of the mass measurement. The end of the pulse provided by one-shot 234 triggers one-shot 236 which in turn provides the clearing signal to the counter 230 after the transfer has been made to latch 232.

When a sample 8 is being inspected, the output of latch 232 is applied through the switch 238 to both the first and second comparators 154 and 160 where the signal is measured to determine whether it is below, between or above the limits set by the lower and upper reference sources 156 and 162 and if without the limits set to subsequently energize the appropriate solenoid, as previously described. The switch 238 is similar to switch 152 of FIG. 6 so that it is open only when the reference object 110 is being inspected and the system stabilized. Thus, the measurement of the mass of object 110 will have no affect on the sorting system which includes the first and second comparators 154 and 160.

The output of latch 232 is connected to the means 106B for stabilizing the system gain. More specifically, the output of latch 232 is connected to subtractor 240. The latter is essentially a comparator for comparing the digital count provided by the output of latch 232 and the stabilization reference count which is set by the operator in the reference source 242. The subtractor is only operative when enabled by an output signal from the reference object light detector 114 provided when the beam 116 is interrupted. When enabled if a difference exists between the output of latch 232 and source 242, a difference signal is applied to the digital integrator 244. The latter integrates the error signals over time to provide a corrective signal to the timer 228 in order to adjust the time signal provided by the timer so that the duration in which the time gate 226 is enabled is either lengthened or shortened, accordingly. The corrective signal thus reduces the error between the digital output of the latch 232 and the stabilization reference count each time the mass of the reference object 110 is measured.

In operation, each product sample 8 is conveyed to the inspection point 10 whereupon it interrupts the light beam 96 causing the light detector 94 to provide an output signal. Again, it is noted that each sample does not interrupt the light beam 116 since the latter lies in a different plane from the sample so that no signal is provided by the reference object light detector 114. At the same time the sample is exposed to the radiation beam 28A so that the sample provides scattered radiation to the radiation detector 20A. The signal output of detector 20A is a series of pulses each of which are applied to the lower and upper discriminators 220 and 222. Those pulses whose amplitudes fall within the predetermined limits set by the discriminators will be passed on to the time gate 226. Since the output of light detector 94 energizes timer 228, the time gate 226 is open for the predetermined period of time set by the timing signal provided by the timer 228. During this period of time, the pulses provided by window gate 224 are counted in counter 230. At the end of a counting period when the timing signal of timer 228 ends and the time gate 226 becomes closed, one-shot 234 is energized providing a transfer pulse to counter 230 so as to transfer the count to the latch 232. A subsequent pulse provided by one-shot 236 clears counter 230. Since reference object light detector 114 has not been energized switch 238 will remain closed, while the subtractor 240 of the stabilization circuit 106B will remain disabled. The signal output of latch 232, representative of the count from counter 230 is provided to the first and second comparators 154 and 160 whereupon the sorting of the samples, in accordance with their measured mass, is accomplished as previously described.

When however, the reference object 110 is conveyed into the inspection point 10, both beams 96 and 116 are interrupted so that both detectors 94 and 114 provide output signals. In the same manner as previously described, the output of detector 94 is applied to the timer 228 which in turn provides a timing signal to the time gate 226 so that the latter is closed for a predetermined period of time. During this time, the series of pulses provided by radiation detector 20A which are within the limits set by the lower and upper discriminators are applied to window gate 224. At the end of the measuring time when the timing signal provided by timer 228 ends, time gate 226 opens and one-shot 234 is activated to provide a transfer pulse to counter 230. The count is then transferred to latch 232 and one-shot 236 is energized to subsequently clear the counter 230.

Since the reference object light detector 114 has been energized, the switch 238 is open and the output of latch 232 will not be applied to the first and second comparators 154 and 160. However, the output of detector 114 will enable the subtractor 240 so that the output of latch 232 can be compared to the stabilization reference count of source 242. Any error between the two signals indicating signal drift, is integrated by the digital integrator 244 and subsequently applied to the timer 228. The time duration in which the timing signal provided by timer 228 is provided will be accordingly adjusted.

As is obvious from the foregoing description to a person skilled in the art, the present invention is capable of quickly and accurately measuring the mass of various products, while periodically standardizing the signal output of the system. Further, by integrating the error signals arising from signal drift any statistical fluctuations in the signal will be substantially cancelled. Additionally, the technique corrects for the decay of the radiation source, particularly gamma ray sources, over long periods of time.

Other advantages and possible modifications of the invention can be made without departing from the invention. For example, the invention has been described as a technique in which the reference object 110 is placed on carousel 72 in place of a product sample 8. Alternatively, every slot 74 can be provided with a product sample 8 and the reference object 110 can be placed between two contiguous samples so long as sufficient measuring time is provided between the measurement of the samples and the reference object. Another alternative is to place the reference object 110 on the side of the sample 8 opposite the radiation source 20 when the sample is located at the inspection point 10. When a product sample is exposed to the beam 28 substantially all the scattered radiation received by the detector will be from the sample. If however, a product sample is not provided at inspection point 10, and the stabilization signal is desired, the beam 28 penetrates the reference object and substantially all the scattered radiation received by the detector will be from the reference object. Finally, the system of FIG. 6 has been described in its preferred form in which system gain is stabilized by adjusting the supply voltage to detector 20 since this technique provides a rather large dynamic range variation. Similarly, in the system of FIG. 7, adjustment of system gain is accomplished by adjusting the time duration in which the time gate is closed. It will be appreciated that the correction signal provided to stabilize the output signal of the system can be accomplished in other ways, such as utilizing the output of converter 188 of FIG. 6 to adjust the amplification factor of amplifier 150, or using the timing output of timer 228 of FIG. 7 to control the opening of a shutter to control the amount of time the product sample or reference object is exposed to beam 28A.

Since certain other changes may be made in the abovedescribed apparatus and method without departing from the scope of the invention herein involved, it is intended that all matter contained in the above description or shown in the accompanying drawings shall be interpreted in the illustrative and not in a limiting sense.

What is claimed is:

1. In an apparatus for inspecting product samples to determine whether each of said samples has a measured quantity of a physical property within predetermined limits, said apparatus comprising means for conveying said samples along a predetermined path through an inspection station; irradiation means disposed adjacent said inspection station for directing a beam of penetrating radiation transversely to said path so that at least a portion of each of said samples is exposed to said beam; detector means adapted to receive radiation scattered by each sample irradiated by said beam; signal generating means responsive to said detector means for generating an electrical signal representative of the amount of radiation received by said detector means in accordance with a predetermined signal gain; and means for determining the quantity of said physical property of each sample irradiated by said beam as a function of said electrical signal; wherein the improvement comprises:

means for periodically exposing at least a portion of a reference object having a predetermined quantity of said physical property to said beam of penetrating radiation, so that (1) said detector means receives radiation from said reference object, and (2) said signal generating means generates a stabilization signal representative of the amount of radiation received from said object by said detector means;

means for providing a predetermined reference signal;

comparison means for comparing said stabilization signal with said reference signal;

means responsive to said comparison means for generating a difference signal representative of the difference between said stabilization and reference signals;

means for integrating said difference signal so as to provide an integrated signal; and means for adjusting said signal gain in response to said integrated signal.

2. Apparatus in accordance with claim 1 wherein said means for conveying said products includes means for conveying said reference object through said inspection station.

3. An apparatus in accordance with claim 2 wherein said reference object is periodically conveyed through said inspection station between two of said samples.

4. An apparatus in accordance with claim 1 wherein said detector means is positioned so as to receive scattered radiation from each of said samples or said reference object irradiated by said beam and said electrical and stabilization signals are representative of the mass of the portion of said sample and said reference object, respectively, from which scattered radiation is received by said detector means.

5. An apparatus in accordance with claim 1 wherein said electrical and stabilization signals are analog signals.

6. An apparatus in accordance with claim 1 further including monitoring means for indicating when said signal gain is not being adequately adjusted.

7. An apparatus in accordance with claim 1 further including means for providing a supply voltage for said detector means, wherein said means for adjusting said signal gain includes means for adjusting said supply voltage level.

8. An apparatus in accordance with claim 1 wherein said means for determining the quantity of said physical property of each of said samples includes means for determining whether said quantity is within a predetermined range.

9. An apparatus in accordance with claim 8 further including sorting means for sorting said samples whose measured quantity of said physical property is within said predetermined range from those samples whose measured quantity of said physical property is outside of said predetermined range.

10. An apparatus in accordance with claim 8 wherein said means for determining the quantity of said physical property is only operative when a sample is positioned in said inspection station and said comparison means is only operative when said reference object is positioned in said inspection station.

11. An apparatus in accordance with claim 10 further including means for distinguishing at said inspection station between said reference object and said product samples and for generating a second electrical signal indicative of the distinction between said reference object and said product samples, and switching means responsive to said second electrical signal for mutually exclusively (1) directing said first mentioned electrical signal representative of the amount of radiation received by said detector means to said means for determining the quantity of said physical property when said each product sample is irradiated by said penetrating beam and (2) directing said stabilization signal to said comparison means when said reference object is irradiated by said penetrating beam.

12. An apparatus in accordance with claim 1 wherein said electrical and stabilization signals are digital signals.

13. An apparatus in accordance with claim 12, wherein said electrical signal and said stabilization signal are each a series of pulses, the pulse repetition rate of each of said series being dependent on the amount of radiation received by said detector.

14. An apparatus in accordance with claim 13, further comprising a counter for counting said pulses of said series of pulses and a time gate for transmitting each of said series of pulses for a predetermined period of time from said detector means, wherein said means for adjusting said signal gain includes means for applying said integrated signal to said time gate so as to adjust said predetermined period of time so that substantially the same number of pulses are transmitted through said time gate each time said reference object is exposed to said beam.

15. An apparatus in accordance with claim 13 further including amplitude discrimination means for excluding from said series of pulses those pulses whose amplitudes are outside of a predetermined limit.

16. A method of stabilizing the signal output of an apparatus for inspecting product samples to determine whether each of said samples has a measured quantity of a physical property within predetermined limits, said method comprising; conveying said samples along a predetermined path through an inspection station; directing a beam of penetrating radiation transversely to said path so that at least a portion of each of said samples is exposed to said beam, detecting radiation scattered by each sample irradiated by said beam, generating an electrical signal representative of the amount of scattered radiation detected in accordance with a predetermined signal gain, wherein the improvement comprises:

periodically exposing at least a portion of a reference object having a predetermined quantity of said physical property to said beam of penetrating radiation;

detecting radiation from said reference object radiated by said beam, generating a stabilization signal in response to the detected radiation from said reference object;

providing a predetermined reference signal;

comparing said stabilization signal with said reference signal;

generating a difference signal representative of the difference between said stabilization and reference signals;

integrating said difference signal so as to provide an integrated signal; and adjusting said signal gain in response to said integrated signal.

17. A method according to claim 16 wherein said reference object is periodically conveyed through said inspection station between two of said samples.

18. A method according to claim 16 wherein the radiation detected from each of said samples and said reference object when irradiated by said beam is scattered radiation and the electrical and stabilization signals are representative of the mass of the portion of said sample and said reference object, respectively, from which scattered radiation is detected.

19. A method in accordance with claim 16 further comprising determining the quantity of said physical property of each of said samples.

20. A method in accordance with claim 19 wherein determining the quantity of said physical property includes determining whether said quantity is within a predetermined range.

21. A method in accordance with claim 20, further comprising sorting said samples whose measured quantity of said physical property is within said predetermined range from those samples whose measured quantity of said physical property is outside said predetermined range.

22. A method in accordance with claim 16 wherein said electrical and stabilization signals are each a series of pulses, the pulse repetition rate of each of said series being dependent on the amount of radiation detected.

23. A method in accordance with claim 22 further comprising counting said pulses of said series for a predetermined period of time and modifying the predetermined period of time in response to said integrated signal.

24. In an apparatus including a source of penetrating radiation, irradiation means for directing a beam of said penetrating radiation toward at least a portion of an exposed sample, detector means positioned relative to said beam and sample so as to receive radiation from said sample when said sample is exposed to said beam and for generating an electrical signal representative of the amount of radiation received by said detector means in accordance with a predetermined signal gain and as a function of a measured quantity of a physical property of said exposed sample, an improved signal stabilization system comprising:

means for exposing to said beam at least a portion of a reference object having a predetermined quantity of said physical property, so that said detector means receives radiation from said reference object and generates a stabilization signal representative of the amount of radiation received by said detector means from said reference object;

means for providing a predetermined reference signal;

comparison means for comparing said stabilization signal with said reference signal and for generating a difference signal representative of the difference between said stabilization and reference signals;

means for integrating said difference signal so as to provide an integrated signal; and means for adjusting said signal gain in response to said integrated signal.

* * * * *